(12) United States Patent
Rossetto et al.

(10) Patent No.: US 7,737,280 B2
(45) Date of Patent: Jun. 15, 2010

(54) PROCESSES FOR PREPARING PALONOSETRON SALTS

(75) Inventors: Pierluigi Rossetto, Lodi (IT); Peter MacDonald, Gentilino (CH); Ettore Bigatti, Rho (IT); Gaia Banfi, Lentate sul Seveso (IT); Dario Tentorio, Vigano (IT)

(73) Assignee: Sicor Inc., Irvine, CA (US)

( * ) Notice: Subject to any disclaimer, the term of this patent is extended or adjusted under 35 U.S.C. 154(b) by 44 days.

(21) Appl. No.: 11/977,419

(22) Filed: Oct. 23, 2007

(65) Prior Publication Data

US 2008/0200681 A1  Aug. 21, 2008

Related U.S. Application Data

(60) Provisional application No. 60/853,840, filed on Oct. 23, 2006, provisional application No. 60/861,488, filed on Nov. 28, 2006, provisional application No. 60/861,847, filed on Nov. 29, 2006, provisional application No. 60/899,102, filed on Feb. 1, 2007, provisional application No. 60/899,109, filed on Feb. 1, 2007, provisional application No. 60/919,165, filed on Mar. 20, 2007, provisional application No. 60/955,679, filed on Aug. 14, 2007.

(51) Int. Cl.
 *C07D 453/02* (2006.01)
(52) U.S. Cl. .................................. 546/133
(58) Field of Classification Search .......... 546/133
 See application file for complete search history.

(56) References Cited

U.S. PATENT DOCUMENTS 5,202,333 A * 4/1993 Berger et al. ............... 514/296
2008/0058367 A1 3/2008 Palle et al.

FOREIGN PATENT DOCUMENTS

EP           0 430 190 A2    6/1991
WO       WO-96-01824 A1     1/1996
WO       WO-2008/073757 A1  6/2008

OTHER PUBLICATIONS

Clark et al., J. Med. Chem. 1993, 36, 2645-2657.*
Xiu et al. Proceedings of international forum on green chemical science & engineering an process systems engineering, Tianjin, china, 1, 2006, 587-590.*
Kowalczyk et al. synthesis, 7, 1996, pp. 816-818.*
Clark, Robin D., et al., "2-(Quinuclidin-3-yl)pyrido[4,3-*b*]indol-1-ones and Isoquinolin-1-ones. Potent Conformationally Restricted H-HT3 Receptor Antagonists", J. Med. Chem., 1933, vol. 36, pp. 2645-2657.
Kowalczyk, Bruce A., et al., "Hydrogenation of Chiral 1*H*-Benz[*de*]isoquinolin-1-one and an Equilibrium Using Palladium Catalyst", Organic Process Research & Development, 1997, vol. 1, pp. 117-120.
Current Opinion in Investigational Drugs, 2002, vol. 3, No. 10, pp. 1502-1507.

* cited by examiner

*Primary Examiner*—D. Margaret Seaman
*Assistant Examiner*—Niloofar Rahmani
(74) *Attorney, Agent, or Firm*—Kenyon & Kenyon LLP

(57) ABSTRACT

The present invention provides processes for preparing Palonosetron salts, especially, the hydrochloride salt and intermediates used to prepare Palonosetron salts.

61 Claims, No Drawings

PROCESSES FOR PREPARING PALONOSETRON SALTS

CROSS REFERENCE TO RELATED APPLICATIONS

The present application claims the benefit of the following U.S. Provisional Patent Application Nos.: 60/853,840, filed Oct. 23, 2006; 60/861,488, filed Nov. 28, 2006; 60/861,847, filed Nov. 29, 2006; 60/899,102, filed Feb. 1,2007; 60/899, 109, filed Feb. 1, 2007; 60/919,165, filed Mar. 20, 2007; and 60/955,679, filed Aug. 14, 2007. The contents of these applications are incorporated herein by reference.

FIELD OF INVENTION

The present invention is directed to processes for preparing Palonosetron salts, especially, the hydrochloride salt.

BACKGROUND OF THE INVENTION

Palonosetron HCl, 1H-Benz[de]isoquinolin-1-one, 2-(3S)-1-azabicyclo[2.2.2]oct-3-yl-2,3,3aS,4,5,6-hexahydro-, monohydrochloride, of the following formula:

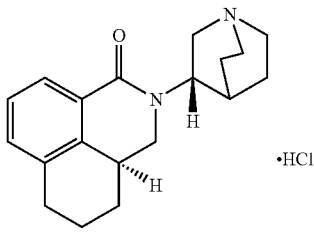

·HCl is a selective 5HT3-antagonist (prevention of chemotherapy-induced nausea and vomiting). It is marketed as a solution under the name Aloxi®. by Helsinn.

Palonosetron HCl and its cyclic amide precursor (referred to as Cp9532) are described in U.S. Pat. No. 5,202,333. Also disclosed is the preparation of Palonosetron HCl by reacting 5,6,7,8-tetrahydronaphthalene-1-carboxylic acid (referred to as Cp20774) with the diamine (referred to as Cp20771) providing the related amide (referred to as Cp9533), which is purified via it's hydrochloride salt (referred to as Cp9563). Then, Cp 9533 reacts with BuLi to provide the cyclic amide (referred to as Cp9532), which is then converted to Palonosetron by hydrogenation process. The process is illustrated by the following scheme:

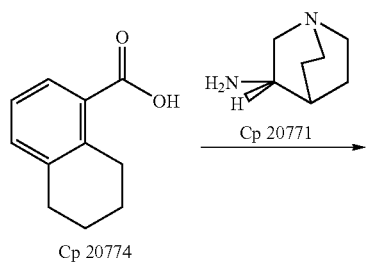

Cp 20774

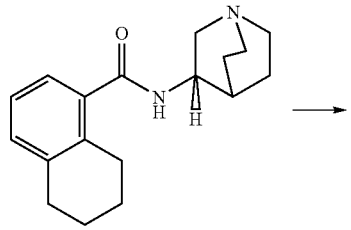

Cp 9533

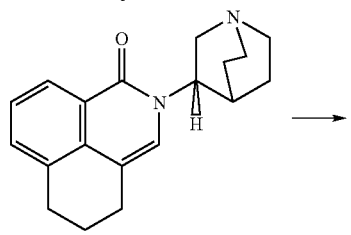

Cp 9532

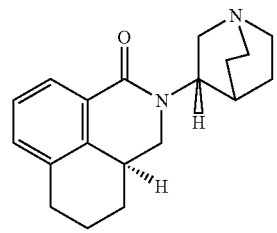

Cp 9502
Palonosetron

The hydrogenation step is done in the presence of a mixture of acids, providing a mixture of Palonosetron salts, which are converted to the base, and then to Palonosetron HCl.

EP patent. No 430190 describes a process similar to the one disclosed in U.S. Pat. No. 5,202,333.

Another similar process is described in J. Med. Chem. 1993, 36, however, in this journal, the hydrogenation is performed on the hydrochloride salt of Cp9532. This hydrogenation is performed in the presence of acids, such as acetic acid and perchloric acid, providing a mixture of Palonosetron salts, which is transformed to Palonosetron free base is and then converted to Palonosetron HCl, providing it in moderate yields.

The hydrogenation step for converting the cyclic amide (referred to as Cp9532) to Palonosetron HCl is described in Organic process Research & development, 1997, 1, 117; wherein the cyclic amide or its salt analogue is used for the reaction. The use of the salt and high amounts of catalyst are described herein, leading to a ratio of about 1:1 of the below depicted isomers. Also reported is the use of the free base form of the amide leading to a better ratio of isomers, but also to Palonosetron contaminated with the starting material, a cyclic amide, an impurity difficult to purify from.

According to the processes described in the above patents and journal articles, Palonosetron HCl is obtained as a mixture of R and S isomers at carbon No. 3. Typically, in the mixture of R and S isomers prepared according to these processes the R and S isomers are present in such mixture in a 1:2.1 to 1:3.3 ratio (see Table 3 of OPRD 1997, 1, 117-120) or 43:57 ratio (when obtained by hydrogenation as hydrochloride) and a 30:70 ratio (when hydrogenating as base) (see J Med Chem, 1993, 36, 2645-2657).

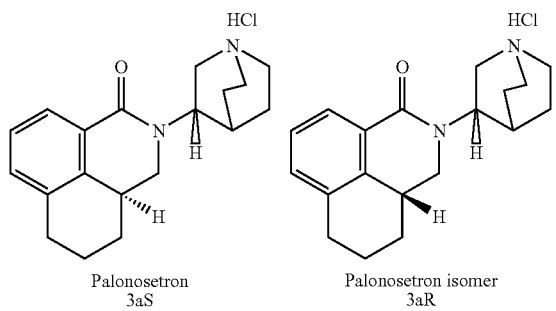

Palonosetron
3aS

Palonosetron isomer
3aR

However, only the 3aS isomer is reported to possess a higher affinity for 5-HT (see Current Opinion in Investigational Drugs 2002 Vol. 3 No 10 page 1502-1507).

Hence, providing a process for producing Palonosetron salt in high yields, high purity, especially from the starting cyclic amide, and with a good isomeric ratio is of benefit.

SUMMARY OF THE INVENTION

In one aspect, the present invention provides a process for preparing (N-[(S)-1-Azabicyclo(2,2,2)oct-3-yl]-5,6,7,8-tetrahydro-1-naphthalene carboxide (the free base of Cp 9563, also known as Cp 9533) of the following formula

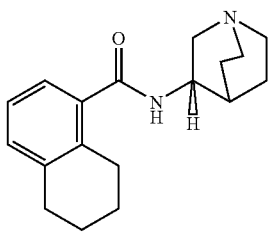

comprising reacting Cp 9588, a salt of Cp 9771 and a base in a solvent mixture comprising water and a water immiscible organic solvent to obtain the free base of Cp 9563.

In another aspect, the present invention provides a process for preparing a Palonosetron salt of the following formula

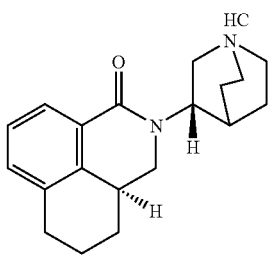

comprising preparing the free base of Cp 9563 by the process of the present invention, and converting it to Palonosetron salt; wherein HC is an acid.

In yet another aspect, the present invention provides a process for preparing a Palonosetron salt of the following formula

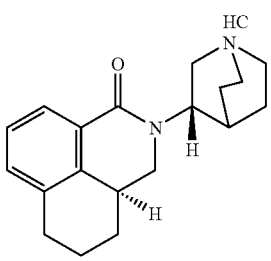

comprising reacting Cp 9558 in an alcohol with not more than 20% by weight of a hydrogenation catalyst per gram of Cp 9558 to obtain Palonosetron salt; wherein HC is an acid.

In one aspect, the present invention provides a process for preparing a Palonosetron salt comprising:

a) reacting Cp 9588,

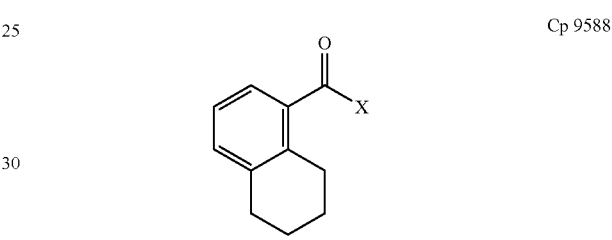

with a salt of Cp 9771

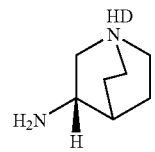

and a base in a solvent mixture comprising water and a water-immiscible organic solvent to obtain the free base of Cp 9563;

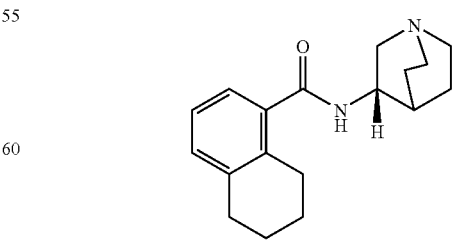

b) reacting the free base of Cp 9563 with a lithium base, thereafter with DMF and then with an acid to obtain Cp 9558;

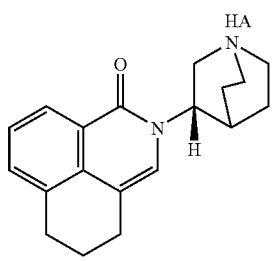

and; c) reacting Cp 9558 in an alcohol with not more than 20% by weight of a hydrogenation catalyst per gram of Cp 9558 to obtain a Palonosetron salt; wherein X is a leaving group excluding OH, and HD is an acid.

In one aspect, the present invention provides a process for preparing a ((S)-2-(1-azabicyclo [2,2,2]oct-3-yl)-2,4,5,6-tetrahydro 1H-benz[de]isoquinolin-1-one salt (Cp 9558) of the following formula

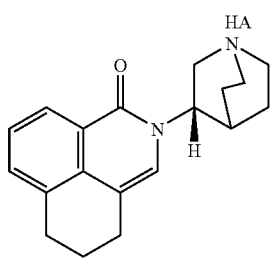

via the (N-[(S)-1-Azabicyclo(2,2,2)oct-3-yl]-5,6,7,8-tetrahydro-1-naphthalene carboxylic acid salt (Cp 9563) of the following formula

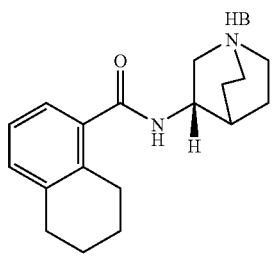

comprising: a) reacting (5,6,7,8-tetrahydro-1-naphthylenecarboxide (Cp 9588) of the following formula

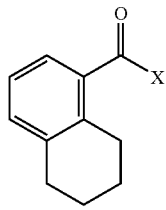

with ((S)-1-Azabicyclo(2,2,2)oct-3-ylamine or (S)-3-aminoquinuclidine (Cp 9771) of the following formula

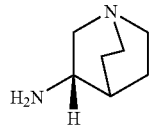

to obtain Cp 9563, and; b) reacting Cp 9563 with a lithium base, thereafter with DMF and then with an acid to obtain Cp 9558; wherein HA and HB are each independently an acid; and X is a leaving group excluding OH.

In another aspect, the present invention provides a process for preparing a Palonosetron salt of the following formula

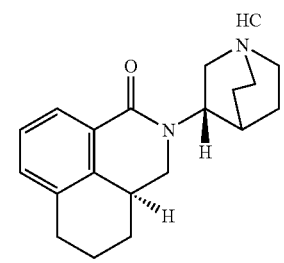

comprising preparing Cp 9558 by the process of the present invention, and converting it to Palonosetron salt; wherein HC is an acid In yet another aspect, the present invention provides a process for preparing a Palonosetron salt comprising: a) reacting the (5,6,7,8-tetrahydro-1-naphthylenecarboxide (referred to as Cp 9588)

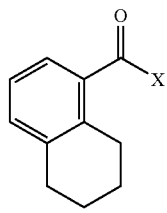

with ((S)-1-Azabicyclo(2,2,2)oct-3-ylamine or (S)-3-aminoquinuclidine (referred to as Cp 9771)

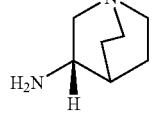

to obtain (N-[(S)-1-Azabicyclo(2,2,2)oct-3-yl]-5,6,7,8-tetrahydro-1-naphthalene carboxylic acid salt (referred to as Cp 9563)

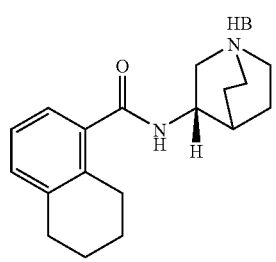

Cp 9563 b) reacting Cp 9563 with a lithium base, thereafter with DMF, and then with an acid to obtain ((S)-2-(1-azabicyclo[2,2,2]oct-3-yl)-2,4,5,6-tetrahydro 1H-benz[de]isoquinolin-1-one salt (referred to as Cp 9558);

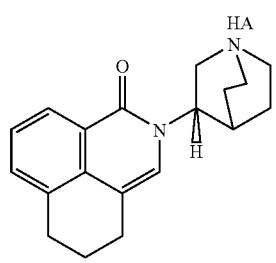

Cp 9558 and; c) reacting Cp 9558 in an alcohol with not more than 20% by weight of a hydrogenation catalyst per gram of Cp 9558 to obtain a Palonosetron salt, where X is a leaving group excluding OH; and HA and HB are each independently an acid.

DETAILED DESCRIPTION OF THE INVENTION

One of the processes provided by the present invention prepares a Palonosetron salt via ((S)-2-(1-azabicyclo[2,2,2]oct-3-yl)-2,4,5,6-tetrahydro 1H-benz[de]isoquinolin-1-one salt (Cp 9558) of the following formula,

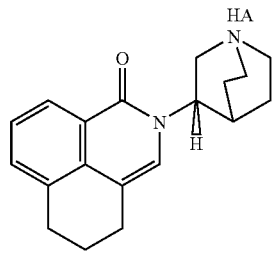

Cp 9558 via (N-[(S)-1-Azabicyclo(2,2,2)oct-3-yl]-5,6,7,8-tetrahydro-1-naphthalene carboxylic acid salt (Cp 9563) of the following formula,

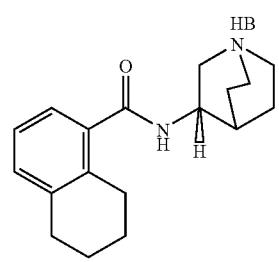

Cp 9563 instead of preparing a Palonosetron salt from the free bases of these intermediates. According to the process of the present invention Cp 9558 is prepared in high purity from Cp 9563 without the need to purify Cp 9563, which is obtained also in high purity by a simple crystallization process.

The process comprises: a) reacting (5,6,7,8-tetrahydro-1-naphthylenecarboxide (referred to as Cp 9588) with ((S)-1-Azabicyclo(2,2,2)oct-3-ylamine or (S)-3-aminoquinuclidine (referred to as Cp 9771) to obtain Cp 9563; b) reacting Cp 9563 with a lithium base, with DMF and then with an acid to obtain Cp 9558; and; c) reacting Cp 9558 in an alcohol with not more than 20% by weight of a hydrogenation catalyst per gram of Cp 9558 to obtain a Palonosetron salt.

The process can be demonstrated by the following scheme:

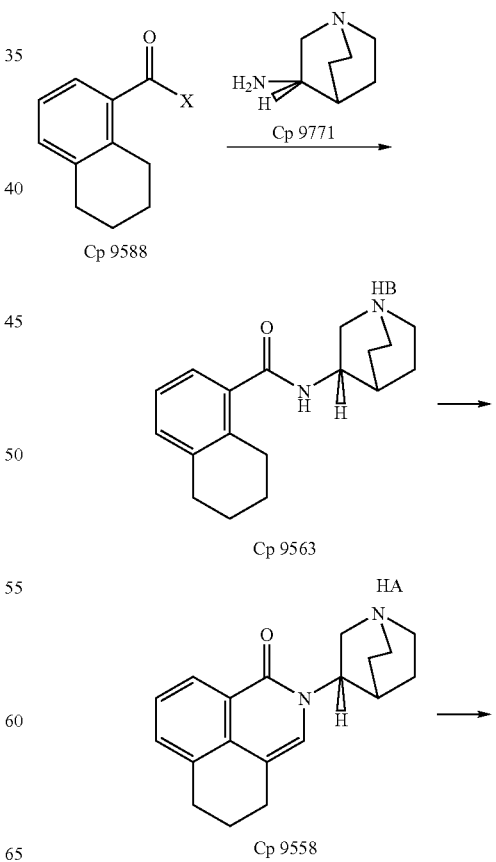

-continued

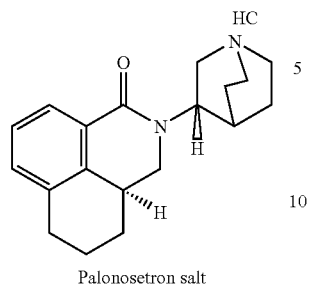

Palonosetron salt wherein HA, HB and HC are each independently an acid; and X is a leaving group excluding OH.

Preferably, X is a leaving group selected from the group consisting of: halogen, OCOR, OCOOR, and $OSO_2R$, wherein R is a $C_1$-$C_4$ alkyl. Preferably, the $C_1$-$C_4$ alkyl is methyl, ethyl, propyl, isopropyl, or butyl. Preferably, X is halogen, more preferably, Cl. Preferably, the acid is selected from the group consisting of: hydrochloric acid, hydrobromic acid, hydrofluoric acid, HI, methylsulfonic acid, toluenesulfonic acid, sulfuric acid, sulfonic acid, nitric acid, acetic acid, trifluoroacetic, trichlroroacetic, and phosphoric acid, more preferably, HCl.

((S)-2-(1-azabicyclo[2,2,2]oct-3-yl)-2,4,5,6-tetrahydro 1H-benz[de]isoquinolin-1-one hydrochloride (referred to as Cp 9558) of the following formula

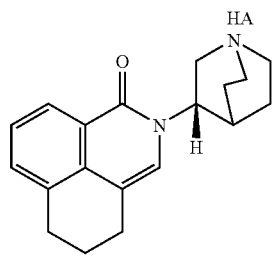

Cp 9558 is prepared via the (N-[(S)-1-Azabicyclo(2,2,2)oct-3-yl]-5,6,7,8-tetrahydro-1-naphthalene carboxylic acid chloride (referred to as Cp 9563) of the following formula.

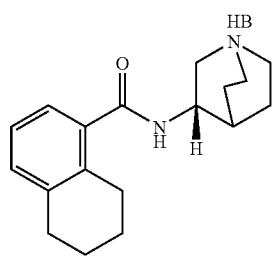

Cp 9563

The process comprises: a) reacting (5,6,7,8)-tetrahydro-1-naphthylenecarboxide (referred to as Cp 9588) of the following formula

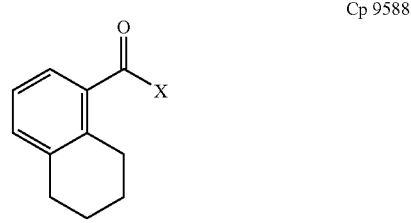

Cp 9588 with ((S)-1-Azabicyclo(2,2,2)oct-3-ylamine or (S)-3-aminoquinuclidine (referred to as Cp 9771) of the following formula

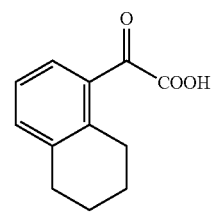

Cp 9771 to obtain Cp 9563; and b) reacting Cp 9563 with a lithium base, thereafter with DMF and with an acid to obtain Cp 9558; wherein HA, HB and X are as described before.

Cp 9588 may be obtained by reacting the acid analogue of Cp 9588 of the following formula

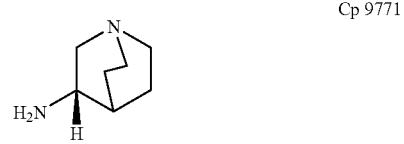

with a substance containing a leaving group, such as a chlorinating agent. The reaction can be done, for example, according to the process described in J. Med Chem. 1993, 36, 2645 (first example) by heating the acid with thionyl chloride in a mixture of dimethylformamide and toluene at about 50° C. for about 1 hour, followed by evaporation. Cp 9771 may be obtained by reacting the acid salt of Cp 9771 with a base, for example, according to the process disclosed in WO 96/01824, for example in example 3 therein.

In one process of the present invention, a solution of Cp 9588, preferably in a $C_{1-4}$ halogenated hydrocarbon, more preferably dichloromethane, a $C_{6-8}$ aromatic hydrocarbon, more preferably toluene, a $C_{2-5}$ ester, more preferably ethyl acetate, and mixtures of toluene and ethyl acetate, most preferably in toluene, is reacted with a solution of Cp 9771, preferably in a $C_{1-4}$ halogenated hydrocarbon, more preferably dichloromethane, a $C_{6-8}$ aromatic hydrocarbon, more preferably toluene, a $C_{2-5}$ ester, more preferably ethyl acetate, and mixtures of toluene and ethyl acetate, most preferably in toluene. Preferably, the solution of Cp 9588 is added to the solution of Cp 9771. This addition is can be carried out at a temperature of about −20° C. to about 60° C., preferably, at about −25° C. to about −5° C., more preferably at about 0° C. to about −5° C. Further, this addition can be a drop-wise addition, preferably, over a period of about 30 minutes to about 1.5 hours. The addition of the two solutions provides a reaction mixture.

In this process of the invention, when the solvent is toluene the temperature should be maintained at a temperature of about −20° C. to 60° C., preferably, at about 20° C. to about 60° C., more preferably at about 40° C. to about 60° C. In addition, when the solvent is dichloromethane the temperature should be maintained at a temperature of about −20° C. to 40° C., preferably, at about −20° C. to about 20° C., more preferably at about 0° C. to about 20° C.

During the addition the temperature of the obtained reaction mixture typically rises. Preferably, the temperature doesn't rise to more than about 20° C. to about 30° C. Where dichloromethane is used as the solvent care should be taken that the temperature does not rise above such temperatures to prevent the formation of degradation products in the reaction, preferably the temperature does not rise to more than about 5° C.

At the end of the addition, the reaction mixture can be heated. Preferably, heating is to a temperature of about 20° C. to about 80° C. Preferably where the solvent is toluene heating is to a temperature of about 70° C. to about 80° C., where the solvent is dichloromethane heating is to a temperature of about 20° C. Preferably, the heating is done for about 30 minutes to about 1.5 hours, more preferably about 30 minutes, to allow the formation of Cp9563 to occur.

Cp 9563 may optionally, be recovered. The recovery can be carried out by any method known in the art, such as filtering and drying. Preferably, Cp 9563 is recovered by concentrating the heated mixture; triturating the concentrate with ethylacetate to obtain a suspension, and filtering the suspension. Preferably, triturating is carried out at about reflux temperature. Preferably, after triturating the suspension is, typically, cooled to increase the yield of the precipitated product. Preferably, cooling is carried out to a temperature of about 0° C. to about 25° C., more preferably of about 15° C. to about 0° C. Preferably, the cooled suspension can be maintained at such temperature for a sufficient period of time to further increase the yield. Preferably, the cooled suspension is maintained for about 30 minutes to about 4 hours, more preferably for about 1 hour, prior to filtering the product.

The obtained Cp 9563 may then be used to prepare Cp 9558 without further purification.

Preferably, a solution or a suspension of Cp 9563 in an ether, preferably a linear, branched or cyclic $C_2$-$C_7$ ether, more preferably, $C_4$-$C_7$ linear, branched or cyclic ether, most preferably in tetrahydrofuran or methyltetrahydrofuran, most preferably in tetrahydrofuran is reacted with the lithium base. Preferably, the lithium base is a $C_1$-$C_{10}$ alkyllithium, more preferably a $C_1$-$C_6$ alkyllithium, most preferably, a $C_4$-$C_6$ alkyllithium. Preferably, the $C_1$-$C_{10}$ alkyllithium is either Hexyllithium or butyllithium. Preferably, a solution of Hexyllithium in hexane is used.

Preferably, the lithium base is used in an amount of about 2 to about 4 mole equivalents, more preferably, of about 3.0 to about 3.5 mole equivalents, even more preferably about 3.1 to about 3.5 mole equivalents per mole equivalent of Cp 9563.

In the process of the invention, the solution of the lithium base is added to the suspension or solution of Cp 9563. Typically, the addition is exothermic, thus the addition is usually, carried out at low temperatures. Preferably, the addition is carried out at a temperature of about −30° C. to about −15° C., more preferably, at about −20° C. to about −25° C. This addition in the process of the invention can be drop-wise, preferably, over a period of about 30 minutes to about 2 hours, more preferably for about a half hour to about 1 hour. Subsequently, dimethylformamide is added. Preferably, the addition is carried out at a temperature of about −15° C. to about −30° C., more preferably, at about −20° C. to about −25° C. This addition in the process of the invention can be drop-wise, preferably, over a period of about 30 minutes to about 2 hours, more preferably for about a half hour to about 1 hour.

Subsequently, the reaction is quenched by the addition of an acid The acid can be an organic or inorganic acid. A suitable organic acid is selected from the group consisting of: methylsulfonic acid, toluenesulfonic acid, sulfonic acid, nitric acid, acetic acid, trifluoroacetic, and trichloroacetic. A suitable inorganic acid is selected from the group consisting of: hydrochloric acid, hydrobromic acid, hydrofluoric acid, HI, sulfuric acid, sulfonic acid, nitric acid, and phosphoric acid. More preferably, the acid is HCl. The acid can be neat or in the form of a solution. Preferably, a solution of the acid is used, more preferably, an aqueous solution.

Preferably, the addition of the acid is carried out drop-wise, more preferably, the rate of the addition is dependent on the resulting reaction temperature so as not to exceed a temperature of 15° C. in the resulting mixture. Typically, the addition of the new mixture to the acid leads to a temperature rise of the reaction mixture. Preferably, the temperature rises to about 10° C. to about 25° C., preferably to about 10° C. to about 20° C., more preferably to about 15° C.

Subsequently, the reaction mixture is maintained at such temperature for a sufficient period of time to allow the formation of Cp9558. Preferably, the reaction mixture is maintained for about 5 minutes to about 30 minutes, more preferably about 15 minutes to about 30 minutes.

Cp 9558 may then be recovered from the reaction mixture. The recovery can be carried out by any method known in the art, such as extraction, or evaporating the solvent. Preferably, Cp 9558 is recovered by adding water to the maintained reaction mixture to obtain a two phase system comprising an organic phase and of an aqueous phase; separating of the aqueous phase; adding a water immiscible organic solvent and an inorganic base to the aqueous phase to obtain a solution of the free base of Cp 9558 of the following formula in the organic phase,

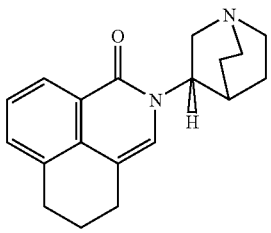

separating the phases; adding an acid and an alcohol to the organic phase; concentrating the resulting mixture to obtain a suspension comprising Cp 9558, and isolating Cp 9558 from the suspension.

Preferably, the water immiscible organic solvent is a halogenated hydrocarbon, ether, ester, or aromatic hydrocarbon. Preferably, the halogenated hydrocarbon is a $C_{1-4}$ halogenated hydrocarbon, more preferably, dichloromethane. Preferably, the ether is a $C_{2-7}$ ether, more preferably a $C_{4-7}$ linear, branched or cyclic ether, even more preferably, diethylether. Preferably the ester is a $C_{2-8}$ ester, more preferably ethyl acetate. Preferably, the aromatic hydrocarbon is a $C_{6-8}$ aromatic hydrocarbon, more preferably, toluene or xylene.

Preferably, the inorganic base is an alkaline hydroxide, most preferably, sodium hydroxide. The base is used in a form of an aqueous solution. Preferably, the addition of the base provides a pH of about 10 to about 12. Preferably, the acid is HCl. Preferably, the acid is in a form of an aqueous solution.

Preferably, after the addition of the acid a mixture is obtained. Preferably, this mixture is concentrated, prior to the addition of the alcohol. Preferably, the alcohol is ethanol, methanol, isopropanol (referred to as IPA), butanol, or pentanol, more preferably ethanol or isopropanol. Preferably, the process of adding the alcohol and concentrating the mixture can be repeated several times, to eliminate any remaining DCM.

Typically, the suspension is cooled to increase the yield of the precipitated Cp 9558. Preferably, the suspension is cooled to a temperature of about 25° C. to about 0° C., more preferably to about 5° C. to about 0° C. Cp 9558 may be recovered from the suspension by filtering it, washing the filtered product, and drying.

The process for preparing Cp 9558 may further comprise a process of converting it to Palonosetron salt of the following formula;

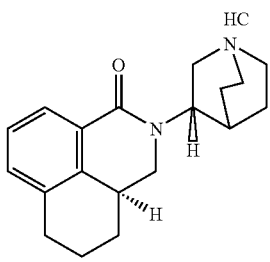

wherein HC is an acid that is described before, preferably, HCl. For example, in the J Med Chem, 1993, 36, 2645 the hydrochloride salt of this compound is hydrogenated (50 psi, 65-70° C.) in acetic acid containing 70% perchloric acid using Pd(OH)$_2$ on carbon. The obtained product has a R to S ratio of 43:57.

The process of the present invention for converting Cp 9558 to Palonosetron salt is done using a suitable solvent which dissolves the starting material and thus promotes the reaction to completion. Moreover, a significantly lower amount of catalyst is used in the process of the invention, leading to an improved isomeric ratio of Palonosetron salt, which is purified without transforming it to the free base, Palonosetron. Also, a recycling process for the desired isomer of Palonosetron salt is provided. Accordingly, the process of the present invention is more cost-effective and efficient.

The process comprises reacting Cp 9558 in an alcohol with no more than 20% by weight of a hydrogenation catalyst per gram of Cp 9558 to obtain Palonosetron salt, preferably, an HCl salt.

Preferably, the alcohol is methanol, ethanol, isopropanol, or butanol, more preferably, methanol. Preferably, the alcohol is anhydrous. Typically, as used herein, the term "anhydrous" refers to a substance containing less than 0.1% by weight of water.

Preferably, the hydrogenation catalyst is selected from the group consisting of PtO$_2$, Rh/Al$_2$O$_3$, Od/BaSO$_4$, and palladium on charcoal, preferably the hydrogenation catalyst is Pd/C. Preferably, the amount of hydrogenation catalyst is of about 1.25% to about 10% by weight per gram of Cp 9558, more preferably, of about 1.25% to about 5% per gram of Cp 9558.

Typically, such reaction is carried out under hydrogen gas pressure. Preferably, the pressure is of about 1 to about 3 atmospheres of hydrogen gas, more preferably, of about 2.5 to about 3 atmospheres.

Preferably, the reaction is performed at a temperature of about 20° C. to about 85° C., more preferably of about 50° C.

to about 82° C. Preferably, the reaction is carried out for about half a day to about 5 days, more preferably for about 1 to about 4 days; during this time the reaction can be monitored by HPLC.

The reaction conducted under the present invention conditions usually consumes the starting material, as determined by HPLC. Moreover, these reaction conditions may also lead to an improved isomeric ratio of the product in the reaction mixture. Preferably, the isomeric ratio is of about 70:30 to about 60:40 of 3aS to 3aR, as determined by HPLC, more preferably, of about 65:35, respectively.

An anti-oxidizing agent in an alcohol may be added to the reaction mixture before recovering Palonosetron salt, thus, preventing from Palonosetron salt to convert back to Cp 9558, from which it is difficult to separate. Preferably, the oxidizing agent is a sulfur compound, such as sulfur dioxide bisulfites, or thiosulfates.

The process for preparing Palonosetron salt may further comprise a recovery process. The recovery of Palonosetron salt may be carried out by any method known in the art, such as evaporating the solvent from the reaction mixture.

The Palonosetron salt may be further purified by crystallizing it from a mixture of an alcohol and water. Preferably, crystallization is carried out by a process comprising dissolving Palonosetron salt in a mixture comprising an alcohol and water, and concentrating the solution to obtain a suspension.

The Palonosetron salt in this crystallization process may be crude Palonosetron salt obtained by the above process or by any other process known to a skilled artisan. Preferably, the alcohol is iso-propanol. Preferably, the suspension is maintained at a temperature of about 10° C. to about 40° C., more preferably of about 20° C. to about 30° C. to increase they yield of the crystallized product. Preferably, the suspension is maintained for about 1 to about 36 hours, more preferably for about 15 to about 20 hours.

The crystallized product can have an isomeric purity of at least 95%, more preferably, of about 95 to 99.5%, most preferably of about 99 to 99.5%, i.e., the 3aS isomer of Palonosetron salt is present in the product mixture in at least 95%. Typically, the purity can be measured by area % units. Preferably, the purity is measured by area % units by HPLC.

The crystallization process may be repeated to increase the isomeric purity. The recrystallized product may have an isomeric purity of at least 99%, i.e., the 3aS isomer of Palonosetron salt is present in the product mixture in at least 99%. Typically, the purity can be measured by area % units. Preferably, the purity is measured by area % units by HPLC.

The 3aS isomer may be recycled from the mother liquor of the crystallization processes by a process comprising evaporating the solvent of the mother liquor to obtain a residue; reacting the obtained residue in an alcohol with no more than 20% by weight of a hydrogenation catalyst per gram of the residue to obtain a mixture enriched with the 3aS isomer, and recovering the recycled 3aS isomer of Palonosetron salt from the enriched mixture. As used herein the term mother liquor refers to a solution or suspension from which a product has been crystallized, here the Palonosetron salt from the above described solution.

Usually, the residue is a mixture of 3aS isomer and 3aR isomer. The mixture may contain about 10% to about 40%, more preferably, of about 10% to about 20% of the 3aS isomer. The reaction of the residue with the hydrogenation catalyst transforms the 3aR isomer into 3aS isomer, thus providing the mixture enriched with the 3aS isomer. After the hydrogenation process the 3aS isomer is present in the reaction mixture in an amount of about 50% to about 75%, preferably of about 60% to about 65%. Typically, the measurement is by area % units. Preferably, the measurement is by area % units by HPLC.

Preferably, the alcohol is methanol, ethanol, isopropanol, or butanol, more preferably, methanol. Preferably, the alcohol is anhydrous.

Preferably, the hydrogenation catalyst is palladium on charcoal. Preferably, the amount of hydrogenation catalyst is used of about 1.25% to about 10% by weight per gram of Cp 9558, more preferably, of about 1.25% to about 5% by weight per gram of Cp 9558.

Preferably, the reaction is done under a pressure of about 1 to about 5 atmospheres of hydrogen gas, more preferably, of about 2.5 to about 3 atmospheres.

Preferably, the reaction is performed at a temperature of about 20° C. to about 85° C., more preferably, of about 50° C. to about 82° C. Preferably, the reaction is carried out for about a half day to about 5 days, more preferably for about 1 to about 4 days.

Preferably, an oxidizing agent is used, as described before, prior to recovering the recycled 3aS isomer. The recovery of the recycled 3aS isomer may be done by any method known in the art, such as evaporating the solvent from the reaction mixture.

The recycled 3aS isomer may be further purified by crystallization from a mixture comprising of an alcohol and water, as described before.

The crystallized 3aS isomer may have an isomeric purity of at least 95%, more preferably, of about 95 to 99.5%, most preferably of about 99 to 99.5%, i.e., the 3aS isomer of Palonosetron salt is present in the product mixture in at least 95%. Typically, the purity can be measured by area % units. Preferably, the purity is measured by area % units by HPLC.

The second process, provided by the present invention prepares Palonosetron salt via the free base of Cp9563, which may be prepared using the Schotten-Baumann conditions, see, Schotten, Ber. Dtsch. Chem. Ges. 1884, 17, 2544. In this process a sufficient amount of a base is used thereby shifting the equilibrium towards the product, Cp9563. Also, Cp9563 is recovered, substantially pure, by a simple extraction-precipitation process, with no need to purify it through its salt.

The process comprises: a) reacting Cp 9588, a salt of Cp 9771 and a base in a solvent mixture comprising of water and a water immiscible organic solvent to obtain the free base of Cp 9563; b) reacting the free base of Cp 9563 with a lithium base, thereafter with DMF and then with an acid to obtain Cp 9558; c) reacting Cp 9558 in an alcohol and with not more than 20% by weight of hydrogenation catalyst per gram of Cp 9558 to obtain Palonosetron salt.

The process can be demonstrated by the following scheme:

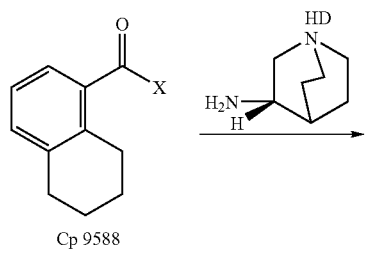

Cp 9588

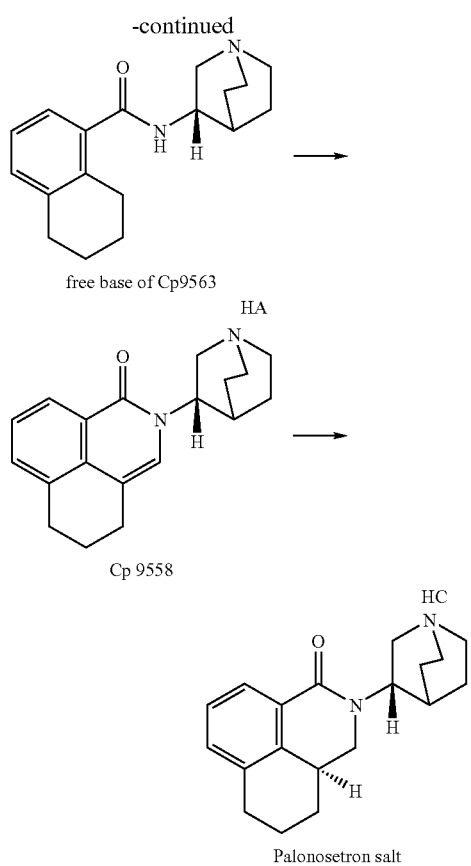

free base of Cp9563

Cp 9558

Palonosetron salt wherein HA, HC and X are as described before and HD is an acid. Preferably, the acid is selected from the group consisting of: hydrochloric acid, sulfuric acid, sulfonic acid, nitric acid, and phosphoric acid, more preferably, HCl.

The free base of Cp 9563 is prepared by a process comprising reacting Cp 9588, a salt of Cp 9771 and a base in a solvent mixture comprising water and a water immiscible organic solvent to obtain the free base of Cp 9563, and optionally recovering the free base of Cp 9563. For use in this process Cp 9588 may be obtained as described before and the salt of Cp 9771 can be obtained from a commercial source.

Preferably, the base is an inorganic base. Preferably, the inorganic base is selected from the group consisting of: alkaline hydroxide, alkaline carbonates, and alkaline hydrogen carbonates. Preferably, the alkaline hydroxide is sodium hydroxide or potassium hydroxide. Preferably, the alkaline carbonate is $Na_2CO_3$ or $K_2CO_3$. Preferably, the alkaline hydrogen carbonates are $KHCO_3$ or $NaHCO_3$.

Preferably, the base is used in an amount of less than about 6 mole equivalent of the starting Cp 9771, more preferably of about 2.9 to about 3.5 mole equivalent per mole of the starting Cp 9771, even more preferably, of about 3 to about 3.1. Preferably, base is in the form of an aqueous solution.

Initially, the aqueous basic solution is admixed with a water immiscible organic solvent. Preferably, the admixing is carried out at a temperature of about 55° C. to about 70° C., more preferably, of about 55° C. to about 60° C.

Preferably, the water immiscible organic solvent is selected from the group consisting of: aromatic hydrocarbons, aliphatic hydrocarbons, halogenated aromatic hydrocarbons, halogenated aliphatic hydrocarbons and ethers, and mixtures thereof. Preferably, the aromatic hydrocarbon is a C$_{6-10}$ aromatic hydrocarbon, more preferably, toluene, benzene or xylene, most preferably, toluene. Preferably, the aliphatic hydrocarbon is a C$_{5-10}$ aliphatic hydrocarbon, more preferably hexane or heptane. Preferably, the halogenated aromatic hydrocarbon is a C$_{5-10}$ halogenated aromatic hydrocarbon, more preferably, chlorobenzene. Preferably, the halogenated aliphatic hydrocarbon is a C$_{6-10}$ halogenated aliphatic hydrocarbon, more preferably, dichloromethane or chloroform, most preferably dichoromethane. Preferably, the ether is a C$_{2-6}$ ether, more preferably, C$_{4-7}$ linear, branched or cyclic ether, even more preferably, 2-methyl-tetrahydrofuran or methylcyclopentyl ether. The most preferred water immiscible organic solvent is toluene.

Typically, when combining water and a water immiscible organic solvent, a two phase system is obtained. This two-phase system is then combined with the salt of Cp9771 to obtain a suspension. The suspension is maintained, preferably, at a temperature of about 20° C. to the reflux temperature of the solvent system, more preferably, of about 20° C. to about 60° C., most preferably, of about 50° C. to about 60° C. Preferably, the suspension is maintained for about 30 minutes to about 2 hours, more preferably about 60 minutes, during which the formation of Cp 9771 occurs.

The obtained suspension is admixed with Cp9588. In the process of the invention Cp9588 is added to the suspension, preferably drop-wise. The addition can be carried out at a temperature of about 30° C. to about 60° C., more preferably to about 60° C. Preferably, the drop-wise addition is carried out over a period of about 1 hour to about 3 hours, more preferably, for about 1 to about 2 hours. The addition of Cp9588 provides a reaction mixture having two phases, an organic phase and an aqueous phase. Preferably, the reaction mixture is maintained at a temperature of about 60° C. for about 30 minutes to about 1 hour, more preferably for about 30 minutes to about 45 minutes; during which the formation of the free base of Cp9563 is expected to occur.

The free base of Cp9563 can then be recovered from the reaction mixture. The recovery can be done by any method known to a skilled artisan. Preferably, the recovery is done by diluting the reaction mixture by addition of another portion of water and of the water immiscible organic solvent, providing a first solvent system comprising an aqueous phase and a water-immiscible organic phase; separating the water-immiscible organic phase from the water phase; washing the water-immiscible organic phase with a basic aqueous solution; concentrating the washed water-immiscible organic phase; admixing it with an aliphatic hydrocarbon; cooling to a temperature of about 15° C. to about 0° C., more preferably of about 5° C. to about 0° C., to obtain a suspension; filtering the suspension; washing the filtered product and drying it.

Preferably, the base is an aqueous solution of an inorganic base. Preferably, the inorganic base is K$_2$CO$_3$, sodium hydroxide, or potassium hydroxide.

Preferably, the water immiscible organic solvent can be the same as the one used for the reaction.

Preferably, the aliphatic hydrocarbon is a C$_{2-8}$ aliphatic hydrocarbon, more preferably, n-heptane, hexane, octane, methylpentane or methylhexane, most preferably, n-heptane.

The process for preparing the free base of Cp9563 may further comprise a process of converting it to Palonosetron salt of the following formula;.

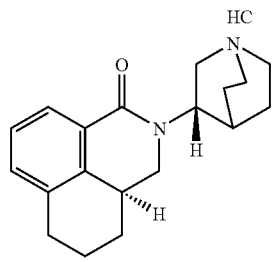

wherein HC is as described before, preferably, HCl. See, for example the disclosure in U.S. Pat. No. 5,202,333, Example 6 or J Med Chem, 1993, 36, 2645-2657 ("Typical Procedure for Conversion of Amides to Fused Pyridones" on page 2653) for methods describes ways that may be used for converting the free base of Cp9558 to Palonosetron HCl.

The conversion of the free base of Cp9563 to Palonosetron salt can be done as described in the first process, where Cp9563 is used, with the difference that less lithium base is used when converting the free base of Cp9563 to Cp9588. Preferably, about 2 to about 2.5, more preferably about 2.0 to about 2.1 mole equivalent of lithium base per mole equivalent of the starting free base of Cp9563 is used in this process.

Having described the invention with reference to certain preferred embodiments, other embodiments will become apparent to one skilled in the art from consideration of the specification. The invention is further defined by reference to the following examples describing in detail the processes of the invention. It will also be apparent to those skilled in the art that many modifications, both to materials and methods, may be practiced without departing from the scope of the invention.

EXAMPLES

HPLC Chromatographic Condition for Analysis of the Purity of Cp9563:

| Column & Packing | Symmetry C18; 5 µm, 250 × 4.6 mm (Waters Part. No. WAT054275) or equivalent | | |
|---|---|---|---|
| Mobile Phase A | 1-Decanesulfonic Acid 20 mM in water, to pH 2.1 with H$_3$PO$_4$ 85% | | |
| Mobile Phase B | Acetonitrile | | |
| | Time (min) | Mobile Phase A (%) | Mobile Phase B (%) |
| Gradient | 0 | 66 | 34 |
| | 15 | 66 | 34 |
| | 25 | 40 | 60 |
| | 35 | 30 | 70 |
| Run Time | 50 minutes | | |
| Post Time | 10 minutes | | |
| Flow Rate | 2.0 mL/min | | |
| Detector | λ = 240 nm | | |
| Column temperature | 60° C. | | |
| Injection Volume | 10 µL | | |

Reaction from Cp9588 to Cp9563.

1. Sample Preparation and Procedure:

Starting Solution Preparation:

Use the mixture reaction solution prepared for the in-process control of step 1 (see method ARPAL08).

Mixture Reaction Preparation:

Add 200 µL of mixture reaction to 12 mL of Methanol. Then add 8 mL of Mobile Phase A.

Then sonicate and inject.

Note: Methyl ester derivate of unreacted Cp9588 is generated when the mixture reaction is added to methanol.

Final Product Preparation:

Prepare a solution containing 1.0 mg/mL of Cp9563 in Acetonitrile/Water 50:50 (v/v).

2. Retention Time:

| | |
|---|---|
| RT of Cp14097 = | about 9.4 minutes |
| RT of Cp9533 = | about 12.2 minutes |
| RT of Cp9588 Methyl Ester Derivative = | about 24.3 minutes |

3. Calculation:

In the chromatogram obtained calculate residual content of Cp309354 in area % by automatic integration. Disregard the peak at about 16 minutes due to Toluene.

HPLC Chromatographic Condition for Measuring the Chemical and Isomeric Purity of Palonosetron HCl

| | | | |
|---|---|---|---|
| Column & Packing | Gemini C18; 3 µm, 150 × 4.6 mm (Phenomenex Part. No. PH00F4439E0) or equivalent | | |
| Mobile Phase A | 0.05% Pyrrolidine in Water (by volume) | | |
| Mobile Phase B | 0.05% Pyrrolidine in Acetonitrile (by volume) | | |
| | Time (min) | Mobile Phase A (%) | Mobile Phase B (%) |
| Gradient | 0 | 67 | 33 |
| | 20 | 67 | 33 |
| | 35 | 40 | 60 |
| | 45 | 40 | 60 |
| Run Time | 45 minutes | | |
| Post Time | 7 minutes | | |
| Flow Rate | 0.9 mL/min | | |
| Detector | λ = 249 nm | | |
| Column temperature | 30° C. | | |
| Injection Volume | 5 µL | | |

Reaction from Cp9558 to Cp9503

1. Sample Preparation and Procedure:

Starting Solution Preparation:

Prepare a solution containing 1.0 mg/mL of Cp9558 in Acetonitrile/Water 50:50 (v/v).

Mixture Reaction Preparation:

Add 200 µL of mixture reaction to 5 mL of Water. Filter (Millex 0.45 µm) and inject.

Final Product Preparation:

Prepare a solution containing 1.0 mg/mL of Cp9503 in Acetonitrile/Water 50:50 (v/v).

2. Retention Time:

RT of Palonosetron 3aR Epimer Analog Cp99569H=about 16.0 minutes

RT of Palonosetron 3,3a-Dehydro HCl Cp99558H (Cp39558)=about 17.3 minutes

RT of Cp9503=about 18.6 minutes

3. Calculation:

In the chromatogram obtained calculate residual content of Cp9558 in area % by automatic integration.

Example 1

Preparation of Cp 9563 (Where it is a hydrochloride Salt) using oxalyl chloride

Preparation of Cp 9771: A 2 L flask was charged with 23.45 g of sodium hydroxide, 250 g of methanol and 58.37 g of (S)-2-aminoquinuclidine di-hydrochloride.

The mixture was heated up to 50° C. for 1 hour under stirring. Then, 500 g of toluene were added, and after 15' of stirring at 30° C. The mixture was filtered, and rinsed with 150 g of toluene.

The collected solution was concentrated under vacuum to a ceros residue, which was dissolved in 250 g of toluene and 100 g of ethyl acetate.

Preparation of Cp 9588 (where X is Cl): In 2 L reactor connected to acid gas scrubber, 665 g of dichloromethane, 2.37 g of DMF and 51.5 g of 5,6,7,8-tetrahydro-1-naphthalene carboxylic acid were charged, followed by a drop-wise addition of 37.5 g of oxalyl chloride.

After 1 hour the mixture was concentrated at 40° under vacuum to give an oil residue, which was dissolved in 665 g of dichloromethane.

Reacting Cp 9771 and Cp 9588: The solution of Cp 9558 was added drop-wise to the stirred solution of (S)-3-aminoquinuclidine in toluene/ethyl acetate cooled to 0°-5°, without exceeding the temperature to more than +5° C.

After about ½ hour the temperature was raised to 20° C. and the mixture was left stirring for 1 hour. The reaction mixture was concentrated under vacuum and the solvent was substituted with 500 g of ethyl acetate. After ½ hour of triturating at the boiling point, the suspension was cooled to 15°-20° and left for one hour to crystallize.

Cp 9563 was filtered, rinsed with cold ethyl acetate.

The product was dried at 50° for 16 hour giving 87.7 g of dry Cp 9563 (yield was 93.2% from more expensive (S)-2-aminoquinuclidine di-hydrochloride). 98% purity by HPLC.

Example 2

Preparation of Cp 9563 (as Free Base) using thionyl chloride

Preparation of Cp 9588 (Where X is Cl):

In a 250 mL glass reactor, under nitrogen atmosphere, 0.24 g of DMF, 310 mL of toluene and 44.8 g of tetrahydronaphthoic acid were charged at room temperature. The suspension was heated to 51±2° C. and 32 g of thionyl chloride were added drop-wise in about 60 minutes. The addition involves the evolution gas.

The solution was stirred at 51±2° C. for 60 minutes. The solvent was then distilled off at reduced pressure with internal temperature 46±2° C. until 210 mL of residual volume (5.1 volumes vs tetrahydronaphtoic acid). The yellowish solution of acyl chloride thus obtained was used with no further purification nor isolation in the following step.

Reacting the Salt of Cp 9771 and Cp 9588:

In a 1000 mL glass reactor, under nitrogen atmosphere, 29.6 g of NaOH pellets and 50 mL of water were charged. The dissolution is highly exothermic. The fluid in the reactor jacket was cooled in order to keep the internal temperature at about 60° C.

To the solution, at 59±2° C., 270 mL of toluene, 42 g of aminoquinuclidine 2HCl were added. The suspension was stirred at 60±2° C. for 60 minutes.

To the suspension, at 60±2° C., the toluenic solution of acyl chloride obtained in step 1 was added dropwise in about 1 hour. After 30 minutes the reaction was considered complete, thus 200 mL of water were added.

120 ml of toluene were then loaded. The suspension was stirred at 53±2° C. for 30 minutes, then the phases were separated. The aqueous phase was eliminated and the organic one was washed with 200 mL of a solution of $K_2CO_3$ 5% in $H_2O$ (prepared dissolving 10 g of $K_2CO_3$ in about 190 ml of $H_2O$).

The organic phase was concentrated under reduced pressure, with internal temperature 55±2° C. until 180 mL of residual volume, diluted with 90 mL of heptane and the suspension was cooled to 0-5° C. The precipitate was collected, rinsed with 40 mL of heptane, and dried under vacuum at 65° C. for 18 hours (96% yield).

Example 3

Preparation of Cp 9558 from Cp 9563 (Where Both are hydrochloride Salt)

A 1 L reactor was charged, under nitrogen atmosphere, with 355 g of tetrahydrofuran and 23.7 g of Cp 9563. The mixture was cooled to −20°-(−)25° C. and 100 ml of 2.5 M hexyl lithium solution in hexane were added drop-wise without exceeding the temperature to more than −15° C. The mixture was kept at −20° C. for a half an hour after complete addition of base, before starting the drop-wise addition of 7 g of DMF.

After another half hour at −20° C., the reaction mixture was added drop-wise to a solution of 56 g HCl 32% and 32 g of water, leaving temperature to rise at about 15° C.

After a half an hour of stirring, the mixture was diluted with 200 g of water and left to separate into 2 phases.

The superior organic phase was eliminated, 300 g of dichloromethane were added to the aqueous phase, and the pH was adjusted to 10.5 by addition of 64 g of 16% aqueous sodium hydroxide. The organic phase was separated, collected and dried using 24 g of sodium sulphate. After filtration and rinsing with dichloromethane, the organic solution was added of 8.4 g of 32% aqueous HCl and concentrated to minimum volume. Then, 237 g of isopropanol were added and the mixture was again concentrated to minimum volume. 237 g of isopropanol were added again and the suspension was concentrated to about 120 ml, cooled to 0° C. and then filtered. The filtered crystals were washed with cold isopropanol, and dried to constant weight at 70° C. under vacuum obtaining 20 5 g (83.9% yield).

Example 4

Preparation of Cp 9558 (Where it is a hydrochloride Salt) from the Free Base of Cp 9563

In a 500 mL glass reactor, under nitrogen atmosphere, 15 g of aminoquinuclidin naphtalen amide and 200 mL of THF were charged at room temperature. The solution was cooled to −25±2° C.

By keeping the temperature below −15±2° C., 54 mL of the solution of hexyl lithium in hexane were added drop-wise in 30 min.

The violet solution was stirred for 20 minutes at T=−20±2° C., then the temperature was lowered to −30±2° C. and 5.9 g of DMF were added in 30 min keeping the temperature below −25° C. The yellowish solution was stirred for 60 minutes at −25±2° C.

To the solution heated to 0±2° C. were then added 15 mL of water and 28.5 g of HCl 37% keeping the temperature below 15° C. After 40 minutes of stirring 120 mL of water were loaded and the mixture was stirred for 20 min at room temperature. The phases were then separated and 130 mL of DCM were added to the aqueous phase containing the hydrochloric salt of the 3-3a dehydro Palonosetron.

To the mixture 28.3 g of a solution of NaOH 15% w/w in water were added (prepared dissolving 4.25 g of NaOH pellets in 24 mL of water). The final pH was 10.5.

The layers were separated and 50 mL of a solution of NaCl 15% w/w in water (prepared dissolving 7.5 g of NaCl pellets in about 42.5 mL of water) were added to the organic phase.

The phases were separated and to the organic one 150 mL of 2-propanol and 6.3 g of HCl 37% were added.

The solvent was distilled off under reduced pressure until 90 mL of residual volume with internal T between 35 and 45° C.

The suspension was heated to 50±2° C. and 100 mL of n-heptane were charged at this temperature.

The suspension was cooled to 0±2° C. in 120 minutes, then after 30 minutes of stirring at this temperature the solid was filtered off washing the cake with a mixture of 15 mL of IPA and 15 mL of n-heptane pre-cooled to 0±2° C.

The solid was dried in oven under vacuum at 70±2° C. for 18 hours, leading to 15.0 g of 3-3a dehydro Palonosetron HCl. HPLC purity about 98%.

Example 5

Preparation of Palonosetron hydrochloride from Cp 9558 (Where it is a hydrochloride Salt) with 1.25% Catalyst 4 g of Cp 9558 was mixed with 120 ml of methanol, and 0.05 g of palladium on charcoal 10%. This mixture was stirred in a hydrogenating reactor.

The mixture was hydrogenated for 4 days at 55° C. under 3 Atmospheres of hydrogen.

After this times no starting material was detected by HPLC and the product had an isomeric ratio of 64/36, 3aS/3aR respectively.

The cooled suspension was added to 1 g of a solution 3.5% of sulphur dioxide in methanol. The suspension was filtered on celite and the filtrate was evaporated to dryness. The residue was dissolved in 80 g of isopropanol and 4 g of water, and the solution was concentrated to half volume, leaving the suspension to crystallize overnight at room temperature.

The precipitate was filtered, washed with a small amount of isopropanol and dried to constant weight at 80° under vacuum.

About 2.3 g of Palonosetron hydrochloride with ~95% isomeric purity were obtained.

Repeating the crystallization from isopropanol about 2 grams of product with 99.2% HPLC isomeric purity were obtained.

Example 6

Preparation of Palonosetron hydrochloride from Cp 9558 (Where it is a hydrochloride Salt) with 2.5% Catalyst 4 g of Cp 9558 were mixed with 120 ml of methanol, and 0.1 g of palladium on charcoal 10%. This mixture was stirred in a hydrogenating reactor.

The mixture was hydrogenated for 2 days at 50° C. under 3 Atmospheres of hydrogen.

After this times, no starting material was detected by HPLC, and the product had an isomeric ratio of 64/36, 3aS/3aR respectively.

The cooled suspension was added to 1 g of a 3.5% solution of sulphur dioxide in methanol. The suspension was filtered on celite and the filtrate was evaporated to dryness. The residue was dissolved in 80 g of isopropanol and 4 g of water, and the solution was concentrated to half volume, leaving the suspension to crystallize overnight at room temperature.

The precipitated was filtered, washed with a small amount of isopropanol and dried to constant weight at 80° C. under vacuum.

About 2.3 g of Palonosetron hydrochloride with 95% isomeric purity were obtained.

Repeating the crystallization from isopropanol about 2 grams of product with 99.1% HPLC isomeric purity were obtained.

Example 7

Preparation of Palonosetron hydrochloride from Cp 9558 (Where it is a hydrochloride Salt) with 5% Catalyst 4 g of Cp 9558 were mixed with 120 ml of methanol, and 0.2 g of palladium on charcoal 10%. This mixture was stirred in a hydrogenating reactor.

The mixture was hydrogenated for 1 day at 50° C. under 2.5 Atmospheres of hydrogen.

After this times no starting material was detectable by HPLC and the product had an isomeric ratio of 61.8/38.2, 3aS/3aR.

The product was isolated as in previous examples with an isomeric purity of 99.6% by HPLC.

Example 8

Preparation of Palonosetron hydrochloride from Cp 9558 (Where it is a hydrochloride Salt) with 5% Catalyst in ethanol 4 g of Cp 9558 were mixed with 240 ml of ethanol, and 0.2 g of palladium on charcoal 10%. This mixture was stirred in a hydrogenating reactor.

The mixture was hydrogenated for 55 hours at 70° C. under 2 Atmospheres of hydrogen.

After this time, no starting material was detected by HPLC and the product had an isomeric ratio of 60.8/39.2, 3aS/3aR, respectively.

After one crystallization from isopropanol as in previous examples, 2.2 g of product were obtained with 95.9% of Palonosetron and 4.1% of its 3aR isomer, while in the mother liquor's the 3aR isomer was 82.1%.

Example 9

Preparation of Palonosetron hydrochloride from Cp 9558 (Where it is a hydrochloride Salt) with 5% Catalyst in 1-butanol 4 g of Cp 9558 were mixed with 200 ml of butanol and 0.2 g of palladium on charcoal 10%. This mixture was stirred in a hydrogenating reactor The mixture was hydrogenated for 55 hours at 90° C. under 2 Atmospheres of hydrogen.

After this time, and the product had an isomeric ratio of 60.2/39.8, 3aS/3aR. After one crystallization from isopropanol as in previous examples, 2.2 grams of product with 93% purity were obtained.

Example 10

Preparation of Palonosetron hydrochloride from Cp 9588 (Where it is a hydrochloride Salt) with 10% Catalyst in methanol In a 500 mL glass autoclave 8 g of Palonosetron 3-3a-dehydro HCl (the 3aS isomer of Cp 9558) and 150 mL of MeOH were charged. 0.8 g of Pd 10% on Carbon, 50% of humidity, were added.

$H_2$ at 4-5 bar was charged.

The suspension was heated to 50° C. and stirred in these conditions for 21 hours (adding $H_2$ when internal pressure <3 bar). The suspension was then cooled to 5±2° C. and 2.56 g of solution of $SO_2$ 5% in water were added to quench the reaction.

After 30 minutes of stirring at this temperature the suspension was filtered over a cake of 10 g of Tecnolite Special 1 washing with 100 mL of MeOH.

First Crystallization:

The solution in MeOH was transferred into a 250 mL reactor and the solvent was distilled off under reduced pressure until 24 mL of residual volume (3 volumes vs Palonosetron 3-3a-dehydro HCl) with internal temperature between 45 and 50° C.

80 mL of 2-propanol were added and the solvent was evaporated until 10 residual volumes (vs Palonosetron 3-3a-dehydro HCl)=80 mL at atmospheric pressure, in order to eliminate MeOH and residual water.

Further 80 mL of 2-propanol were added and the yellow suspension was concentrated until 10 residual volumes=80 mL.

At reflux temperature (79° C.) 4 mL of water and 0.26 g of HCl 37% were added, obtaining a solution of IPA with about 5% of $H_2O$.

The solution was cooled to 0±2° C. in 300 minutes. After 30 minutes of stirring at 0±2° C. The solid was filtered off washing the cake with 20 mL of 2-propanol pre-cooled to 0±2° C. The solid was squeezed on the filter funnel for 1 hour.

3.45 g of crude wet Palonosetron HCl were obtained as pale yellowish solid. HPLC purity about 95.5%, isomeric purity 95.5%.

Second Crystallization:

The wet solid after the first crystallization was loaded into a 250 mL reactor and 80 mL of 2-propanol and 4 mL of water were charged (total about 10 volumes vs Palonosetron 3-3a-dehydro HCl of IPA/5% $H_2O$). The suspension was heated to reflux temperature (79° C.) until dissolution, then cooled to 0±2° C. in 300 minutes. After 30' of stirring at 0±2° C. The solid was filtered off and the cake was washed with 20 mL of 2-propanol pre-cooled to 0±2° C. The solid was squeezed on the filter funnel for 1 hour.

3 g of wet Palonosetron HCl were obtained as white solid. HPLC purity about 98.8%, and the same isomeric purity. The wet solid was dried at 70° C. for a 18 hours under vacuum, leading to 2.9 g of Palonosetron HCl.

We claim:

1. A process for preparing N-[(S)-1-Azabicyclo(2,2,2)oct-3-yl]-5,6,7,8-tetrahydro-1-naphthalene carboxamide (the free base of Cp 9563) of the following formula

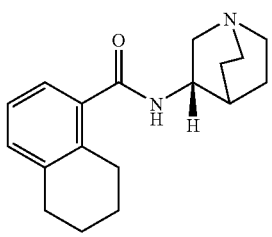

comprising reacting a (5,6,7,8)-tetrahydro-1-naphthylen-ecarboxide (Cp 9588) having the formula,

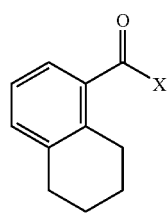

Cp 9588 a salt of (S)-3-aminoquinuclidine (Cp 9771) having the formula:

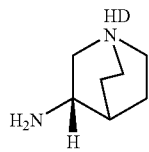

and an inorganic base in a solvent mixture comprising water and a water-immiscible organic solvent to obtain said N-[(S)-1-Azabicyclo(2,2,2)oct-3-yl]-5,6,7,8-tetrahydro-1-naphthalene carboxamide;
wherein X is a leaving group selected from the group consisting of: halogen, OCOR, OCOOR, and $OSO_2R$, wherein R is a $C_1$-$C_4$ alkyl, and HD is an acid; wherein the inorganic base is selected from the group consisting of alkaline hydroxide, alkaline carbonates, and alkaline hydrogen carbonates.

2. The process according to claim 1, wherein the acid is selected from the group consisting of: hydrochloric acid, hydrobromic acid, hydrofluoric acid, HI, methylsulfonic acid, toluenesulfonic acid, sulfuric acid, sulfonic acid, nitric acid, acetic acid, trifluoroacetic, trichloroacetic and phosphoric acid.

3. The process according to claim 2, wherein the $C_1$-$C_4$ alkyl is methyl, ethyl, propyl, isopropyl, or butyl.

4. The process according to claim 2, wherein the halogen is Cl and the acid is HCl.

5. The process according to claim 1, wherein the inorganic base is sodium hydroxide or sodium bicarbonate.

6. The process according to claim 1, wherein the amount of base in the reaction is less than about 6 mole equivalents per mole of (S)-3-aminoquinuclidine salt Cp 9771.

7. The process according to claim 6, wherein the amount of base in the reaction is of about 2.9 to about 3.5 mole equivalents per mole of (S)-3-aminoquinuclidine salt Cp 9771.

8. The process according to claim 1, wherein the base is in the form of an aqueous solution to which the water-immiscible organic solvent is added, at a temperature of about 55° C. to about 70° C.

9. The process according to claim 1, wherein the water immiscible organic solvent is selected from the group consisting of aromatic hydrocarbons, aliphatic hydrocarbons, halogenated aromatic hydrocarbons, halogenated aliphatic hydrocarbons, ethers, and mixtures thereof.

10. The process according to claim 9, wherein the water immiscible organic solvent is selected from the group consisting of $C_{6-10}$ aromatic hydrocarbon, $C_{5-10}$ aliphatic hydrocarbon, $C_{5-10}$ halogenated aromatic hydrocarbon, $C_{6-10}$ halogenated aliphatic hydrocarbon, $C_{4-7}$ linear, branched or cyclic ether, and mixtures thereof.

11. The process according to claim 10, wherein the water immiscible organic solvent is selected from the group consisting of toluene, benzene, xylene, hexane, heptane, chlorobenzene, dichloromethane, chloroform, 2-methyl-tetrahydrofuran, methylcyclopentyl ether, and mixtures thereof.

12. The process according to claim 11, wherein the water immiscible organic solvent is toluene.

13. The process according to claim 1, wherein the salt of (S)-3-amino-quinuclidine Cp 9771 is added to the mixture of the aqueous basic solution and the water immiscible organic solvent to obtain a suspension, and the suspension is heated to a temperature of about 20° C. to about reflux temperature.

14. The process according to claim 13, wherein Cp 9588 is added to the suspension at a temperature of about 50° C. to about 70° C. to obtain a reaction mixture.

15. The process according to claim 1, wherein the free base of N-[(S)-1-aza-bicyclo(2,2,2)oct-3-yl]-5,6,7,8-tetrahydro-1-naphthalene carboxamide Cp 9563 is recovered.

16. The process according to claim 15, wherein recovery of the free base of N-[(S)-1-azabicyclo(2,2,2)oct-3-yl]-5,6,7,8-tetrahydro-1-naphthalene carboxamide Cp9563 comprises:
a) diluting the reaction mixture containing the free base of N-[(S)-1-azabicyclo(2,2,2)oct-3-yl]-5,6,7,8-tetrahydro-1-naphthalene carboxamide Cp9563 with water and the water-immiscible organic solvent forming a two phase system,
b) separating the organic phase from the aqueous phase,
c) washing the organic phase with an aqueous basic solution,
d) concentrating the organic phase,
e) admixing the organic phase with an aliphatic hydrocarbon to form a mixture,
f) cooling the mixture to a temperature of about 0° C. to about 5° C. to obtain a suspension, and
g) filtering the suspension to obtain the free base of N-[S)-1-azabicyclo(2,2,2)oct-3-yl]-5,6,7,8-tetrahydro-1-naphthalene carboxamide Cp 9563.

17. The process according to claim 1, further comprising converting the free base of N-[(S)-1-azabicyclo(2,2,2)oct-3-yl]-5,6,7,8-tetrahydro-1-naphthalene carboxamide Cp 9563 to a Palonosetron salt of the following formula:

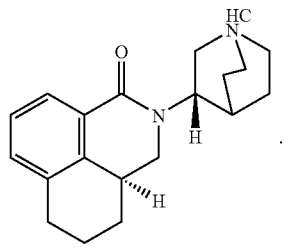

18. The process according to claim 17, wherein the free base of N-[(S)-1-azabicyclo(2,2,2)oct-3-yl]-5,6,7,8-tetrahydro-1-naphthalene carboxamide Cp 9563 is converted to a Palonosetron salt, said process comprising:

a) reacting the free base of N-[(S)-1-azabicyclo(2,2,2)oct-3-yl]-5,6,7,8-tetrahydro-1-naphthalene carboxamide Cp 9563 with a lithium base, thereafter with DMF, and then with an acid to obtain (S)-2-(1-azabicyclo[2,2,2]oct-3-yl)-2,4,5,6-tetrahydro 1H-benz[de]isoquinolin-1-one salt (Cp 9558);

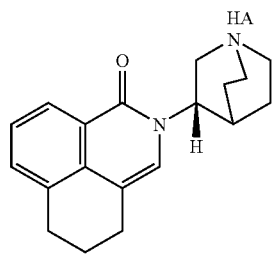

and;

c) reacting (S)-2-(1-azabicyclo[2,2,2]oct-3-yl)-2,4,5,6-tetrahydro 1H-benz[de]isoquinolin-1-one salt Cp 9558 in an alcohol with not more than 20% by weight of a hydrogenation catalyst per gram of (S)-2-(1-azabicyclo[2,2,2]oct-3-yl)-2,4,5,6-tetrahydro 1H-benz[de]isoquinolin-1-one salt Cp 9558 to obtain said Palonosetron salt; wherein HA and HC are each independently an acid.

19. The process according to claim 17, wherein the acid is selected from the group consisting of hydrochloric acid, hydrobromic acid, hydrofluoric acid, HI, methylsulfonic acid, toluenesulfonic acid, sulfuric acid, sulfonic acid, nitric acid, acetic acid, trifluoroacetic, trichloroacetic, and phosphoric acid.

20. The process according to claim 19, wherein the acid is HCl.

21. The process according to claim 18, wherein the alcohol is selected from the group methanol, ethanol, isopropanol, butanol.

22. The process according to claim 18, wherein the alcohol is anhydrous.

23. The process according to claim 18, wherein the hydrogenation catalyst is selected from the group consisting of PtO$_2$, Rh/Al$_2$O$_3$, Od/BaSO$_4$, and Pd/C (palladium on charcoal).

24. The process according to claim 18, wherein the amount of the hydrogenation catalyst is from about 1.25% to about 10% by weight (gram) of the (S)-2-(1-azabicyclo[2,2,2]oct-3-yl)-2,4,5,6-tetrahydro 1H-benz[de]isoquinolin-1-one salt Cp 9558.

25. The process according to claim 24, wherein the amount of the hydrogenation catalyst is from about 1.25% to about 5% by weight (gram) of the (S)-2-(1-azabicyclo-[2,2,2]oct-3-yl)-2,4,5,6-tetrahydro 1H-benz[de]isoquinolin-1-one salt Cp 9558.

26. The process according to claim 18, wherein the reaction is carried out under a hydrogen gas pressure of about 1 to about 3 atmosphere of the hydrogen gas.

27. The process according to claim 18, wherein the reaction is carried out at a temperature of about 50° C. to about 85° C.

28. The process according to claim 18, further comprising crystallizing the obtained Palonosetron salt.

29. The process according to claim 28, wherein the crystallization of the Palonosetron salt is repeated.

30. A process for preparing a (S)-2-(1-azabicyclo[2,2,2]oct-3-yl)-2,4,5,6-tetrahydro 1H-benz[de]isoquinolin-1-one salt (Cp 9558) of the following formula

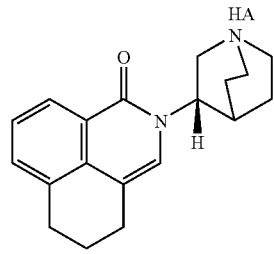

from the [(S)-1-Azabicyclo(2,2,2)oct-3-yl]-5,6,7,8-tetrahydro-1-naphthalene carboxamide salt (Cp 9563) of the following formula

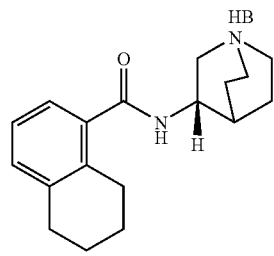

comprising:
a) reacting the (5,6,7,8)-tetrahydro-1-naphthylenecarboxide (Cp 9588) intermediate, having the formula,

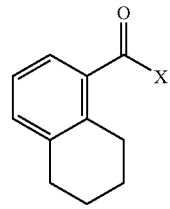

with (S)-3-aminoquinuclidine (Cp 9771)

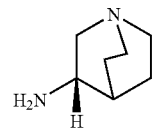

to obtain said N-[(S)-1-azabicyclo(2,2,2)oct-3-yl]-5,6,7,8-tetrahydro-1-naphthalene carboxamide salt Cp 9563; and b) reacting said N-[(S)-1-azabicyclo(2,2,2)oct-3]-5,6,7,8-tetrahydro-1-naphthalene carboxamide salt Cp 9563 with a lithium base, thereafter with DMF and then with an acid to obtain (S)-2-(1-azabicyclo[2,2,2]oct-3-yl)-2,4,5,6-tetrahydro 1H-benz[de]isoquinolin-1-one salt Cp 9558, wherein HA and HB are each independently an acid; and X is a leaving group selected from the group consisting of: halogen, OCOR, OCOOR, and OSO$_2$R, wherein R is a C$_1$-C$_4$ alkyl.

31. The process according to claim 30, wherein the leaving group X is selected from the group consisting of: halogen, OCOR, OCOOR, and OSO$_2$R, wherein R is a C$_1$-C$_4$ alkyl, and the acid is selected from the group consisting of: hydrochloric acid, hydrobromic acid, hydrofluoric acid, HI, methylsulfonic acid, toluenesulfonic acid, sulfuric acid, sulfonic acid, nitric acid, acetic acid, trifluoroacetic, trichloroacetic, and phosphoric acid.

32. The process according to claim 31, wherein the C$_1$-C$_4$ alkyl is methyl, ethyl, propyl, isopropyl, or butyl.

33. The process according to claim 31, wherein the halogen is Cl and the acid is HCl.

34. The process according to claim 30, wherein step (a) is done by adding a solution of the (5,6,7,8)-tetrahydro-1-naphthylenecarboxide intermediate to a solution of (S)-3-aminoquinuclidine Cp 9771 at a temperature of about −20° C. to about 60° C. to obtain a reaction mixture.

35. The process according to claim 34, wherein the solutions of the (5,6,7,8)-tetrahydro-1-naphthylenecarboxide intermediate Cp 9588 and (S)-3-aminoquinuclidine salt Cp 9771 are in toluene, dichloromethane, ethylacetate or in a mixture of toluene and ethylacetate.

36. The process according to claim 34, further comprising heating the resulting reaction mixture to about 20° C. to about 80° C., to obtain N-[(S)-1-azabicyclo(2,2,2)oct-3-yl]-5,6,7,8-tetrahydro-1-naphthalene carboxamide Cp 9563.

37. The process according to claim 34, further comprising recovering N-[(S)-1-azabicyclo(2,2,2)oct-3-yl]-5,6,7,8-tetrahydro-1-naphthalene carboxamide Cp 9563 from the reaction mixture.

38. The process according to claim 30, wherein a solution of N-[(S)-1-azabicyclo(2,2,2)oct-3-yl]-5,6,7,8-tetrahydro-1-naphthalene carboxamide Cp 9563 in an ether is used in step (b).

39. The process according to claim 38, wherein the ether is a linear, branched or cyclic C$_{4-7}$ ether.

40. The process according to claim 39, wherein the linear, branched or cyclic C$_{2-7}$ ether is either tetrahydrofuran or methyltetrahydrofuran.

41. The process according to claim 30, wherein the lithium base in step (b) is a C$_{1-10}$ alkyllithium base.

42. The process according to claim 41, wherein the C$_{1-10}$ alkyllithium base is either hexyllithium or butyllithium.

43. The process according to claim 30, wherein an amount of about 2 to about 4 mole equivalents of the lithium base per mole of N-[(S)-1-azabicyclo(2,2,2)oct-3-yl]-5,6,7,8-tetrahydro-1-naphthalene carboxamide Cp 9563 is used in step (b).

44. The process according to claim 30, wherein the lithium base is added at about −30° C. to about −15° C.

45. The process according to claim 30, wherein the acid in step b) is selected from the group consisting of methylsulfonic acid, toluenesulfonic acid, sulfonic acid, nitric acid, acetic acid, trifluoroacetic, trichloroacetic, hydrochloric acid, hydrobromic acid, hydrofluoric acid, HI, sulfuric acid, sulfonic acid, nitric acid, and phosphoric acid.

46. The process according to claim 45, wherein the acid is hydrochloric acid.

47. The process according to claim 30, further comprising recovering (S)-2-(1-azabicyclo[2,2,2]oct-3-yl)-2,4,5,6-tetrahydro 1H-benz[de]isoquinolin-1-one salt Cp 9558 by a process comprising the steps of:
a) adding water to a reaction mixture containing (S)-2-(1-azabicyclo[2,2,2]oct-3-yl)-2,4,5,6-tetrahydro 1H-benz[de]isoquinolin-1-one Cp 9558 obtained in step b) to obtain a two phase system of an organic phase and an aqueous phase;
b) adding a water immiscible organic solvent and an inorganic base to the aqueous phase to obtain the free base of (S)-2-(1-azabicyclo[2,2,2]oct-3-yl)-2,4,5,6-tetrahydro 1H-benz[de]isoquinolin-1-one Cp 9558 in an organic phase;
c) adding an acid and an alcohol to the organic phase containing the free base of (S)-2-(1-azabicyclo[2,2,2]oct-3-yl)-2,4,5,6-tetrahydro 1H-benz[de]isoquinolin-1-one Cp 9558 to obtain (S)-2-(1-azabicyclo[2,2,2]oct-3-yl)-2,4,5,6-tetrahydro 1H-benz[de]isoquinolin-1-one salt Cp 9558;
d) concentrating the organic phase to obtain a suspension; and
d) isolating the (S)-2-(1-azabicyclo[2,2,2]oct-3-yl)-2,4,5,6-tetrahydro 1H-benz[de]-isoquinolin-1-one salt Cp 9558 from the suspension.

48. The process according to claim 30, further comprising converting the (S)-2-(1-azabicyclo[2,2,2]oct-3-yl)-2,4,5,6-tetrahydro 1H-benz[de]isoquinolin-1-one salt (Cp 9558) obtained in step b) to a Palonosetron salt.

49. The process according to claim 48, wherein the Palonosetron salt is Palonosetron hydrochloride.

50. A process for preparing a Palonosetron salt comprising:
a) providing a (S)-2-(1-azabicyclo[2,2,2]oct-3-yl)-2,4,5,6-tetrahydro 1H-benz[de]isoquinolin-1-one salt (Cp 9558), and
b) reacting said (S)-2-(1-azabicyclo[2,2,2]oct-3-yl)-2,4,5,6-tetrahydro 1H-benz[de]isoquinolin-1-one salt Cp 9558 in an alcohol with not more than 20% by weight of a hydrogenation catalyst per gram of (S)-2-(1-azabicyclo[2,2,2]oct-3-yl)-2,4,5,6-tetrahydro 1H-benz[de]isoquinolin-1-one salt Cp 9558 to obtain a Palonosetron salt of the following formula:

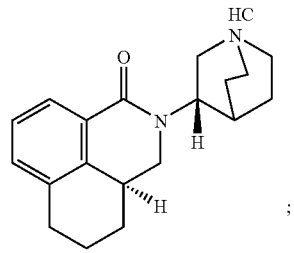

wherein HC is an acid.

51. The process according to claim 50, wherein the Palonosetron salt is Palonosetron hydrochloride.

52. The process according to claim 50, wherein providing (S)-2-(1-azabicyclo[2,2,2]oct-3-yl)-2,4,5,6-tetrahydro 1H-benz[de]isoquinolin-1-one salt Cp 9558 comprises preparing Cp 9558 according to a process that comprises reacting a (5,6,7,8)-tetrahydro-1-naphthylenecarboxide (Cp 9588) having the formula,

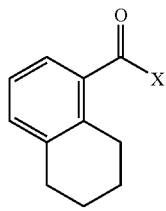

Cp 9588 a salt of (S)-3-aminoquinuclidine (Cp 9771) having the formula:

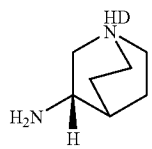

and an inorganic base in a solvent mixture comprising water and a water-immiscible organic solvent to obtain said (N-[(S)-1-Azabicyclo(2,2,2)oct-3-yl]-5,6,7,8-tetrahydro-1-naphthalene carboxamide; wherein X is a leaving group selected from the group consisting of: halogen, OCOR, OCOOR, and $OSO_2R$, wherein R is a $C_1$-$C_4$ alkyl, and HD is an acid; wherein the inorganic base is selected from the group consisting of alkaline hydroxide, alkaline carbonates, and alkaline hydrogen carbonates.

53. The process according to claim 50, wherein the alcohol is selected from the group consisting of methanol, ethanol, isopropanol and butanol.

54. The process according to claim 50, wherein the alcohol is anhydrous.

55. The process according to claim 50, wherein the hydrogenation catalyst is selected from the group consisting of $PtO_2$, $Rh/Al_2O_3$, $Od/BaSO_4$, and Pd/C (palladium on charcoal).

56. The process according to claim 50, wherein the amount of the hydrogenation catalyst is from about 1.25% to about 10% by weight (gram) of the (S)-2-(1-azabicyclo[2,2,2]oct-3-yl)-2,4,5,6-tetrahydro 1H-benz[de]isoquinolin-1-one salt Cp 9558.

57. The process according to claim 56, wherein the amount of the hydrogenation catalyst is from about 1.25% to about 5% by weight (gram) of the (S)-2-(1-azabicyclo-[2,2,2]oct-3-yl)-2,4,5,6-tetrahydro 1H-benz[de]isoquinolin-1-one salt Cp 9558.

58. The process according to claim 50, wherein the reaction is carried out under a hydrogen gas pressure of about 1 to about 3 atmosphere of the hydrogen gas.

59. The process according to claim 50, wherein the reaction is carried out at a temperature of about 50° C. to about 85° C.

60. The process according to claim 50, further comprising crystallizing the obtained Palonosetron salt.

61. The process according to claim 60, wherein the crystallization of the Palonosetron salt is repeated.

* * * * *

UNITED STATES PATENT AND TRADEMARK OFFICE
CERTIFICATE OF CORRECTION

PATENT NO. : 7,737,280 B2  Page 1 of 1
APPLICATION NO. : 11/977419
DATED : June 15, 2010
INVENTOR(S) : Rossetto et al.

It is certified that error appears in the above-identified patent and that said Letters Patent is hereby corrected as shown below:

Column 27
Line 46, change "Od/BaSO$_4$" to --Os/BaSO$_4$--

Column 32
Line 8, change "Od/BaSO$_4$" to --Os/BaSO$_4$--

Signed and Sealed this

Twenty-eighth Day of September, 2010

David J. Kappos
*Director of the United States Patent and Trademark Office*